United States Patent
Isshiki (10) Patent No.: US 12,096,958 B2
(45) Date of Patent: Sep. 24, 2024

(54) SOFT-THREAD CANNULA AND CANNULA SEAL ASSEMBLY

(71) Applicant: Conmed Corporation, Utica, NY (US)

(72) Inventor: Ryo Isshiki, Largo, FL (US)

(73) Assignee: Conmed Corporation, Utica, NY (US)

( * ) Notice: Subject to any disclaimer, the term of this patent is extended or adjusted under 35 U.S.C. 154(b) by 581 days.

(21) Appl. No.: 17/415,371

(22) PCT Filed: Dec. 27, 2019

(86) PCT No.: PCT/US2019/068728
§ 371 (c)(1),
(2) Date: Jun. 17, 2021

(87) PCT Pub. No.: WO2020/140025
PCT Pub. Date: Jul. 2, 2020

(65) Prior Publication Data
US 2022/0054164 A1    Feb. 24, 2022

Related U.S. Application Data (60) Provisional application No. 62/786,085, filed on Dec. 28, 2018, provisional application No. 62/785,331, filed on Dec. 27, 2018.

(51) Int. Cl.
*A61B 17/34*    (2006.01)

(52) U.S. Cl.
CPC ...... *A61B 17/3421* (2013.01); *A61B 17/3439* (2013.01); *A61B 17/3496* (2013.01);
(Continued)

(58) Field of Classification Search
CPC ............ A61B 17/3421; A61B 17/3496; A61B 17/3417; A61B 17/3439; A61B 17/3423;
(Continued)

(56) References Cited

U.S. PATENT DOCUMENTS 5,630,805 A * 5/1997 Ternamian ......... A61B 17/3421
                                                  604/274
5,993,471 A   11/1999 Riza et al.
(Continued)

FOREIGN PATENT DOCUMENTS

CN    206261645 U    6/2017
EP    3202346          8/2017
(Continued)

OTHER PUBLICATIONS

International Search Report Form PCT/ISA/210, International Application No. PCT/US2019/068728, pp. 1-15 Dated, Mar. 20, 2020.
(Continued)

*Primary Examiner* — Mohamed G Gabr
*Assistant Examiner* — Aman Kumar Mann
(74) *Attorney, Agent, or Firm* — Bond, Schoeneck & King, PLLC; Frederick J.M. Price (57) ABSTRACT

A cannula seal assembly with a compatible flexible cannula. The cannula includes a rigid cannula body having proximal and distal body ends. The cannula body is composed of material having a first thickness. A flexible thread extends along at least a portion of the cannula body from the distal body end toward the proximal body end. The thread is composed of material having a second thickness, which is less than a first thickness. The cannula is attachable to a cannula seal assembly. The assembly includes a housing having a primary seal and a secondary seal therein. The assembly has a spacer connected between the primary seal and the secondary seal and a reservoir between the primary seal and the secondary seal.

8 Claims, 14 Drawing Sheets

(52) U.S. Cl.
CPC ... *A61B 2017/3419* (2013.01); *A61B 17/3423* (2013.01); *A61B 2017/3458* (2013.01)

(58) Field of Classification Search
CPC .... A61B 2017/3419; A61B 2017/3458; A61B 2017/00862; A61B 17/3498; A61B 2017/348; A61B 2017/349; A61B 17/3462; A61B 17/34; A61B 17/3415; A61B 2017/3454

See application file for complete search history.

(56) References Cited

U.S. PATENT DOCUMENTS

| | | | |
|---|---|---|---|
| 5,997,515 | A | 12/1999 | De La Torre et al. |
| 8,506,475 | B2 | 8/2013 | Brannon |
| 10,219,799 | B2 | 3/2019 | Pattison et al. |
| 2004/0230161 | A1 | 11/2004 | Zeiner |
| 2010/0100045 | A1* | 4/2010 | Pravongviengkham ............ A61B 17/3421 604/164.01 |
| 2010/0268024 | A1* | 10/2010 | Brannon ............ A61B 17/3421 600/104 |
| 2011/0196206 | A1 | 8/2011 | Hammond |
| 2014/0135585 | A1* | 5/2014 | Albrecht ............ A61B 17/3423 600/204 |
| 2015/0065808 | A1* | 3/2015 | Van Wyk ............ A61B 17/3462 600/201 |
| 2015/0094543 | A1* | 4/2015 | Whittaker .......... A61B 17/3431 600/208 |
| 2016/0166359 | A1* | 6/2016 | Flach .................. A61C 8/0022 433/174 |
| 2019/0008614 | A1* | 1/2019 | Weitzel .................... A61C 8/00 |
| 2019/0307937 | A1* | 10/2019 | Fitzgerald .......... A61B 17/3421 |
| 2020/0268445 | A1* | 8/2020 | Hancock ............ A61B 18/1815 |

FOREIGN PATENT DOCUMENTS

| | | |
|---|---|---|
| KR | 200465473 | 2/2013 |
| WO | 2007093957 A2 | 8/2007 |
| WO | 2018/094458 | 5/2018 |

OTHER PUBLICATIONS

EP search report, reference EPA-52789, EP Application No. 23163295.1-1113, pp. 1-8, Dated Jun. 6, 2023.

Notice of Preliminary Rejection, dated Jul. 11, 2023, Application No. 10-2021-7023566, pp. 1-6.

JP Office Action, App. No. 2021-537077, dated Jul. 6, 2022, pp. 1-11.

* cited by examiner

SOFT-THREAD CANNULA AND CANNULA SEAL ASSEMBLY

CROSS-REFERENCE TO RELATED APPLICATION

This application is a national stage application under 35 U.S.C. 371 based on international patent application PCT/US19/68728 filed on Dec. 27, 2019, which claims priority to and the benefit of U.S. Provisional Patent Application Ser. No. 62/785,331 filed on Dec. 27, 2018 and entitled "Cannula Seal Mechanism," and U.S. Provisional Patent Application Ser. No. 62/786,085, filed on Dec. 28, 2018 and entitled "Soft-Thread Cannula," the entireties of which are incorporated herein by reference.

BACKGROUND OF THE INVENTION

1. Field of the Invention

The present invention relates to a surgical device and assembly and, more particularly, to a cannula seal assembly with a compatible flexible cannula.

2. Description of Related Art

Cannulas are used to support arthroscopic or endoscopic procedures by providing access to portals to the surgical site. Due to issues of fluid management, cannulas are often equipped with a seal at the proximal end. The seal limits fluid flow through the cannula, but may also contribute to the development of fluid pressure. Disturbing the seal by passing instruments or devices through the cannula may lead to spontaneous and uncontrolled projectile fluid leaks.

Further, traditional cannulas often have a rigid body with rigid threads. The rigid body maintains a tube-like structure for passing instruments and devices, while the rigid threads grab the tissue at the surgical site and provide fixation of the cannula. However, the rigid threads on cannula bodies can cause additional trauma and risk of injury at the surgical site when the cannula is inserted.

Therefore, there is a need for a cannula with flexible features for reducing injury and a seal assembly for controlling the outflow of fluid from a surgical site when passing instruments to the surgical site.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention are directed to a cannula seal assembly with a compatible flexible cannula. According to one aspect, the present invention is a cannula including a rigid cannula body having a proximal body end and distal body end. The cannula body is composed of material having a first thickness. A flexible thread extends along at least a portion of the cannula body from the distal body end toward the proximal body end. The thread is composed of material having a second thickness, which is less than a first thickness.

According to another aspect, the cannula includes a rigid cannula body having a proximal body end and a distal body end. A flexible sleeve extends along at least a portion of the cannula body from the distal body end toward the proximal body end. The cannula also includes a flexible thread extending along at least a portion of the sleeve.

According to another aspect, the present invention is a cannula seal assembly. The assembly includes a housing having a primary seal and a secondary seal therein. The assembly has a spacer connected between the primary seal and the secondary seal and a reservoir between the primary seal and the secondary seal.

These and other aspects of the invention will be apparent from and elucidated with reference to the embodiment(s) described hereinafter.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which.

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
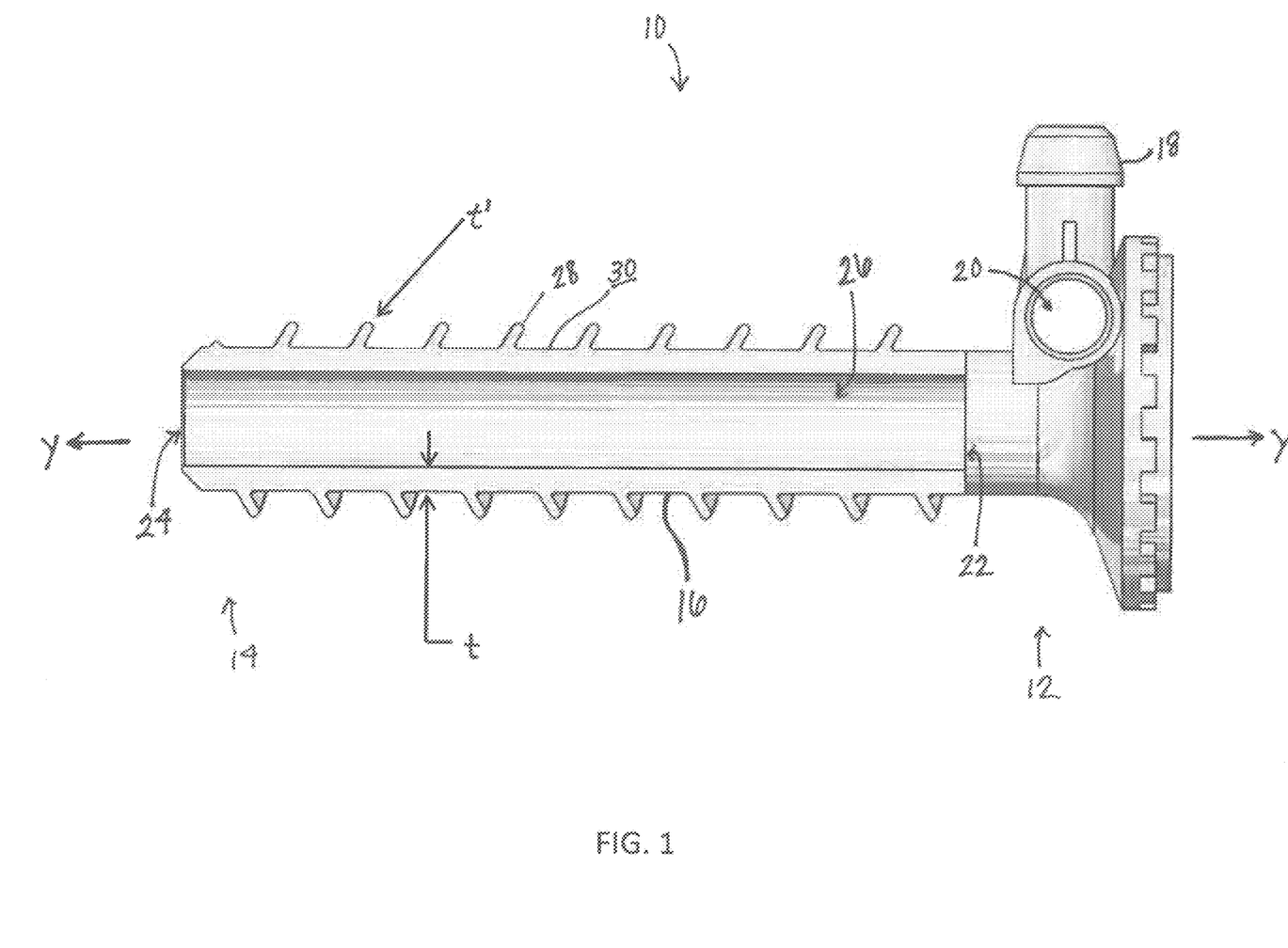
FIG. 1 is a partial sectional view schematic representation of a cannula, according to an embodiment.

Referring now to the figures, wherein like reference numerals refer to like parts throughout, FIG. 1 shows a partial sectional view schematic representation of a cannula 10, according to an embodiment. The cannula 10 has a proximal end 12 and a distal end 14. The distal end 14 is configured for insertion into a portal at a surgical site. A cannula body 16 extends from the proximal end 12 to the distal end 14 along a central longitudinal y-y axis. The cannula 10 additionally includes a port 18 extending from its proximal end 12. The port 18 provides an exit for the flow of fluid from the cannula 10. The port 18 includes a control valve (not shown) for allowing or prohibiting the flow of fluid through the port 18. (The control valve would extend through a control valve aperture 20, as understood by a person of ordinary skill in the art).

The cannula body 16 is elongated and tubular, having an open proximal body end 22 and an open distal body end 24 with an inner volume 26 extending therebetween. The inner volume 26 is sized and configured to accommodate surgical instruments and devices. In the depicted embodiment, the distal body end 24 of the cannula body 16 is threaded such that a thread 28 extends proximally along at least a portion of an exterior surface 30 of the cannula body 16 from its distal body end 24, as shown. The thread 28 functions as a fixation feature for anchoring the cannula 10 at the surgical site.

Figure 2:
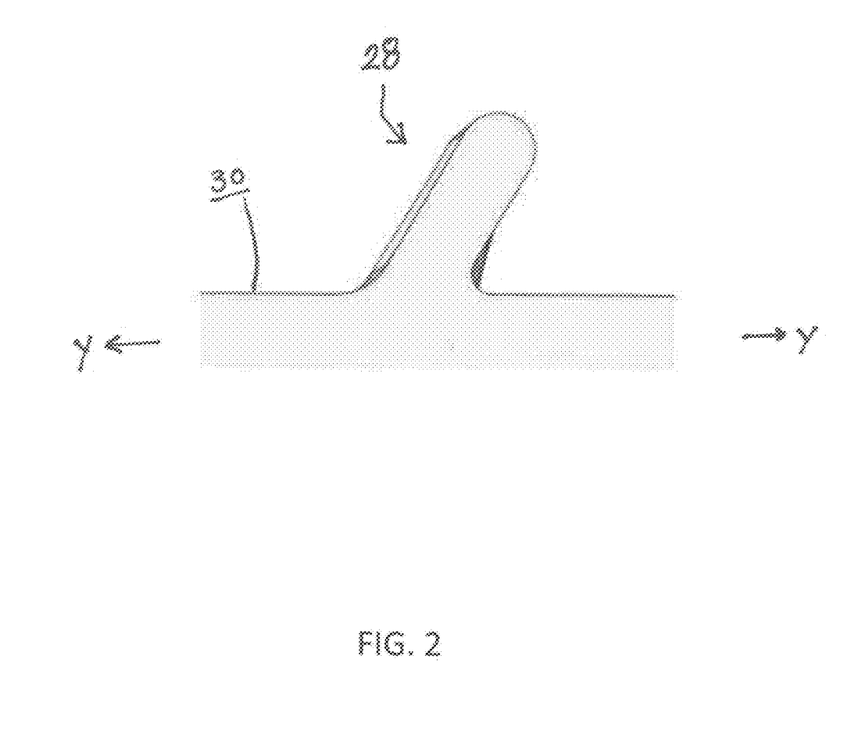
FIG. 2 is a close-up sectional side view schematic representation of the thread, according to an embodiment

Turning now to FIG. 2, there is shown a close-up sectional side view schematic representation of the thread 28, according to an embodiment. As shown, the thread 28 extends at an angle relative to the central longitudinal y-y axis. In particular, the thread 28 extends proximally (i.e., toward the proximal end 12 of the cannula 10). The profile of the thread 28 is angled in the proximal direction, away from the direction of insertion. In an alternative embodiment, the profile of the thread 28 can be angled in the distal direction, toward the direction of insertion.

Figure 3:
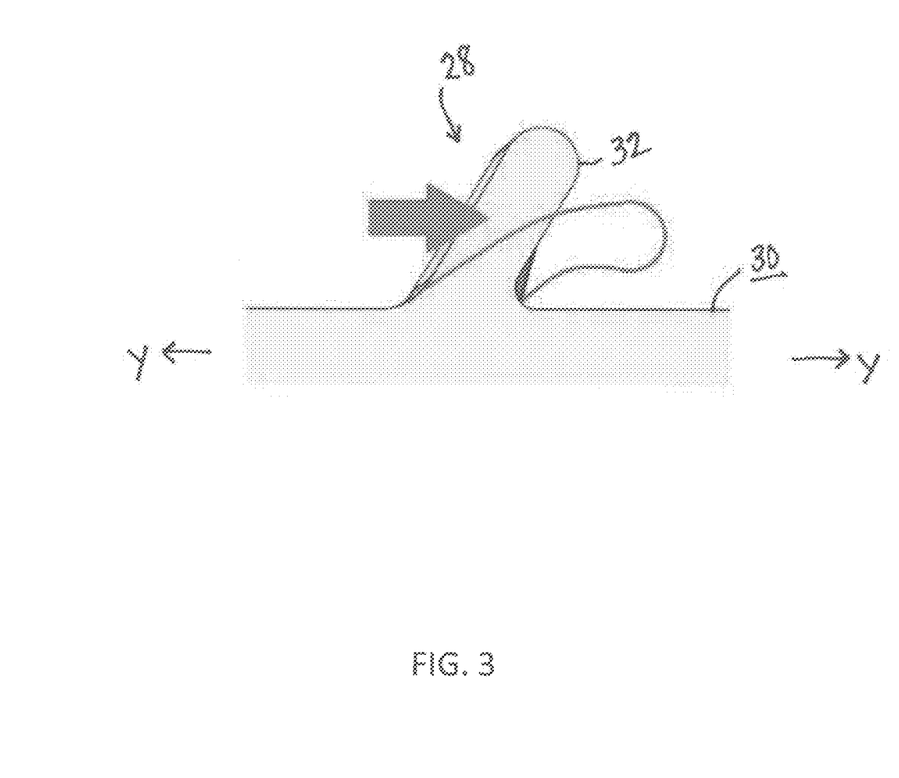
FIG. 3 is a close-up sectional side view schematic representation of the thread in a compressed position, according to an embodiment.

Referring now to FIG. 3, there is shown a close-up sectional side view schematic representation of the thread 28 in a compressed position, according to an embodiment. As shown, the thread 28 is composed of flexible material such that the thread 28 yields under a predetermined compression force. In other words, a tip 32 of the thread 28 bends toward the exterior surface 30 of the cannula body 16 in the proximal direction (toward the central longitudinal y-y axis) to a compressed position. This bending in the proximal direction reduces the overall profile of the cannula 10 when it is compressed during insertion (i.e., when force is applied in the proximal direction by tissue). Thus, the smaller profile of the thread 28 during insertion minimizes interference.

Figure 4:
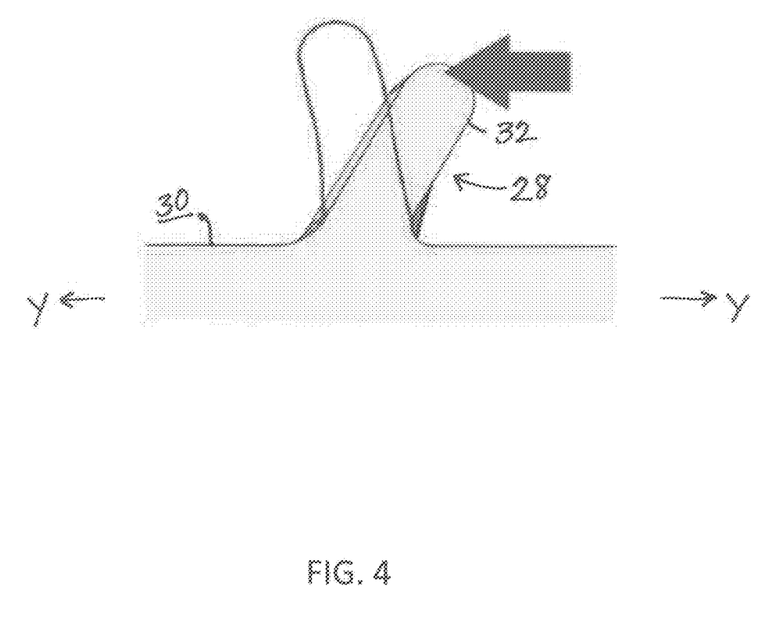
FIG. 4 is a close-up sectional side view schematic representation of the thread in an expanded position, according to an embodiment.

Turning now to FIG. 4, there is shown a close-up sectional side view schematic representation of the thread 28 in an expanded position, according to an embodiment. Although the thread 28 is flexible, the thread 28 must be able to provide fixation at the surgical site. As shown in FIG. 4, the thread 28 expands under tensile load (i.e., force in the distal direction) to maximize the overall profile of the cannula 10 during usage. Thus, the larger profile of the thread 28 during usage increases the fixation strength of the cannula 10 in the tissue at the surgical site. From the compressed position in FIG. 3, the tip 32 of the thread 28 bends back slightly in the distal direction to an expanded position.

Figure 5:
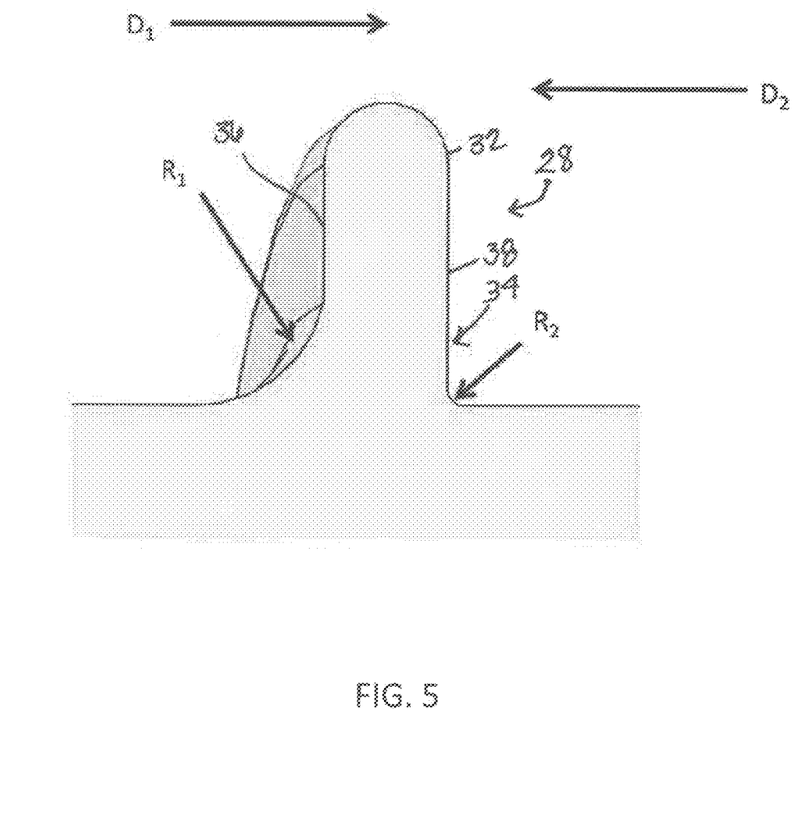
FIG. 5 is a close-up sectional side view schematic representation of the thread, according to an alternative embodiment.
Figure 6:
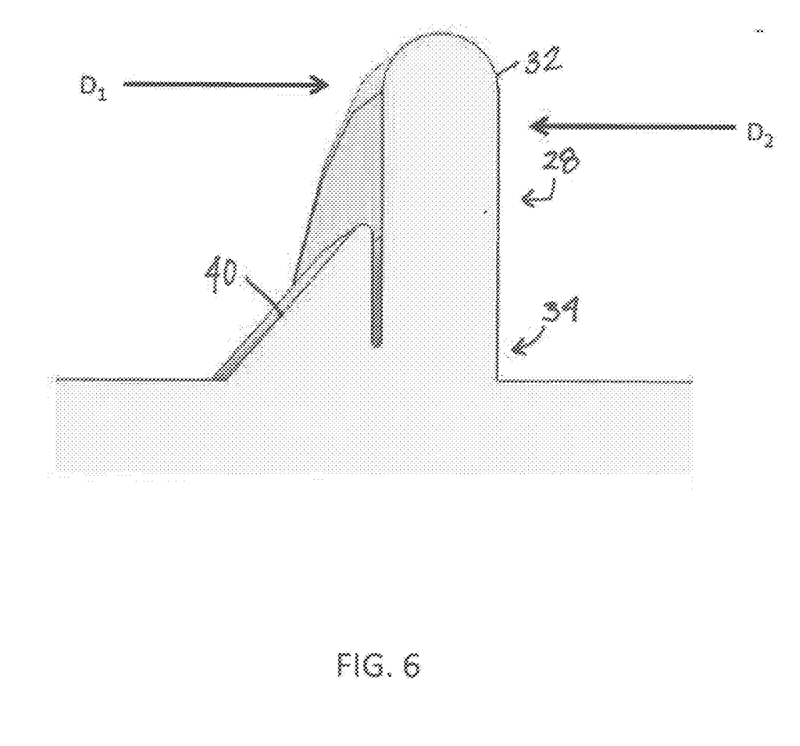
FIG. 6 is a close-up sectional side view schematic representation of the thread, according to another alternative embodiment.

Referring now to FIGS. 5 and 6, there are shown close-up sectional side view schematic representations of the thread 28, according to alternative embodiments. In the embodiments shown in FIGS. 5 and 6, the geometry of the thread 28 allows for compression in the proximal direction and resistance to compression in the distal direction. In FIG. 5, the thread 28 has different radii at a base 34 of the thread 28. Specifically, the thread 28 has a first radius $R_1$ on distal side 36 of the base 34 and a second radius $R_2$ on a proximal side 38 of the base 34. In the depicted embodiment, the second radius $R_2$ is smaller than the first radius $R_1$. With a smaller second radius $R_2$ on the proximal side 38, the thread 28 is more susceptible to being compressed in the proximal direction $D_1$. Similarly, with a larger first radius $R_1$ on the distal side 36, the base 34 is more resistant to compression in the distal direction $D_2$.

In FIG. 6, the thread 28 has a reinforced base 34 that resists compression in the distal direction $D_2$. In the depicted embodiment, the thread 28 has a supporting feature 40, such as a secondary thread, adjacent to the distal side 36 of the base 34 (or thread 28). In FIG. 6, the supporting feature 40 has a triangular cross-section. In particular, the supporting feature 40 is angled such that it is larger (or wider) closer to the thread 28. The angle of the supporting feature 40 allows the tip 32 of the thread 28 to be compressed in the proximal direction $D_1$ (i.e., it does not interfere with force applied in the distal direction $D_1$) and supports the base 34 of the thread 28 when force is applied to the thread 28 in the proximal direction $D_1$. Furthermore, the supporting feature 40 is small enough that it does not extend past the thread 28 when the thread 28 is in the compressed position.

The combination of rigid and flexible features in the cannula 10 may be achieved using a single material or a combination of materials. The cannula 10 in FIG. 1 is composed of a single material. The combination of rigid and flexible features of the cannula 10 can be achieved by optimizing the material property of the substrate and the geometry of the cannula 10. In the embodiment of the cannula 10 shown in FIG. 1, the cannula body 16 has a tube thickness t. The thickness t is large enough that the use of a flexible material can still create a rigid cannula body 16. Similarly, the same material can be used for the flexible thread 28 by varying the thickness of the material. As shown in FIG. 1, the thread 28 has a thickness t' that is small enough that the thread 28 is pliable. In the depicted embodiment, the thickness t' of the thread 28 is less than the thickness t of the cannula body 16.

Figure 7:
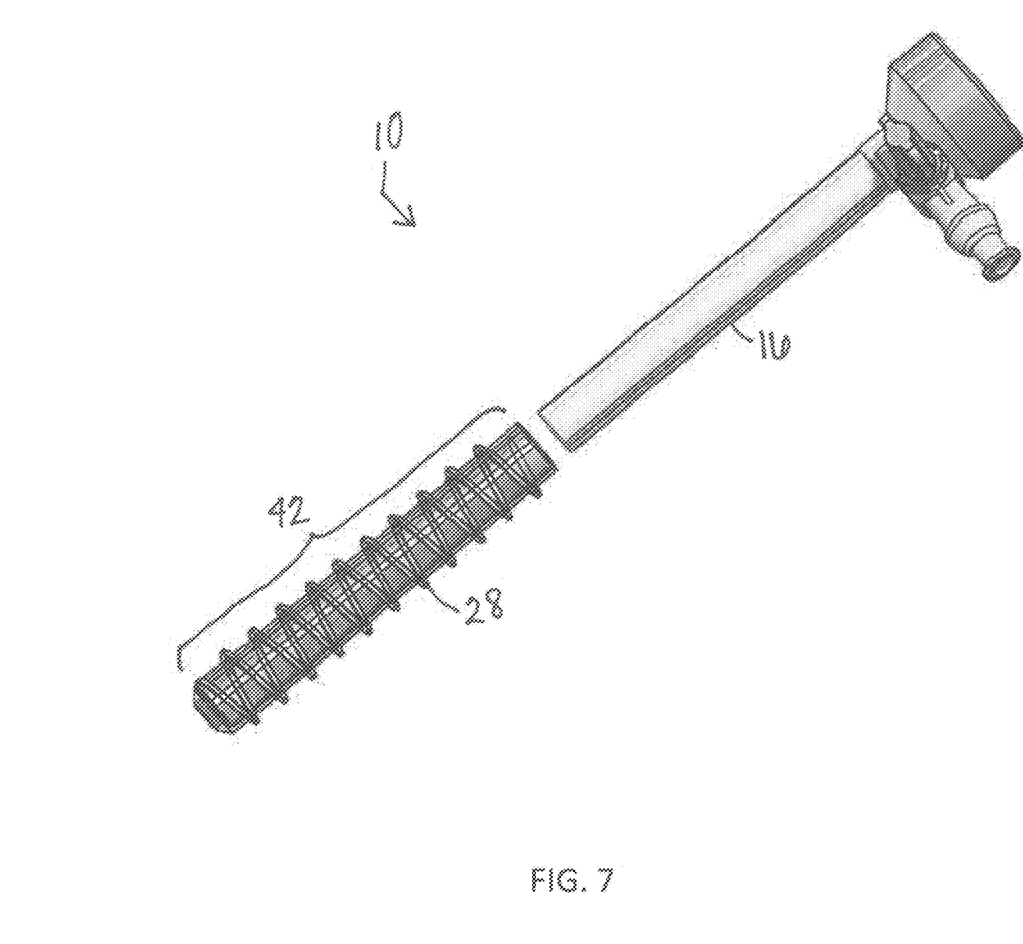
FIG. 7 is a partial exploded view schematic representation of a cannula, according to an alternative embodiment.
Figure 8:
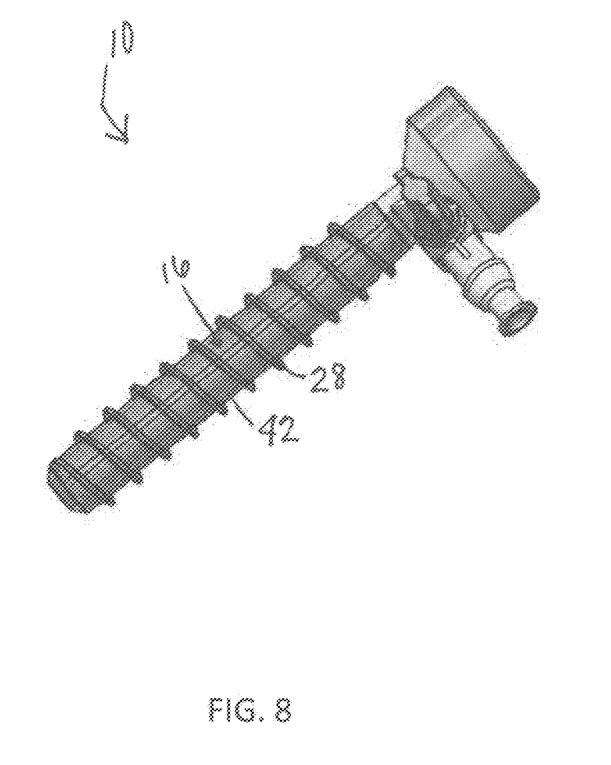
FIG. 8 is a perspective view schematic representation of the cannula of FIG. 7.

Referring now to FIGS. 7 and 8, there are shown partial exploded and perspective views schematic representations of a cannula 10, according to an alternative embodiment. The cannula 10 shown in FIGS. 7 and 8 is composed of a combination of materials. In other words, some features of the cannula 10 are composed of flexible material, while other features of the cannula 10 are composed of rigid material. As shown in FIG. 7, the cannula body 16 is fabricated from or otherwise composed of a rigid material, which provides the structural strength of the cannula 10.

On the other hand, the thread 28 is fabricated from or otherwise composed of a flexible material, which provides the pliability required for decreasing interference during insertion. In the embodiment shown in FIGS. 7 and 8, the thread 28 is fabricated on a sleeve 42 composed of flexible material. The sleeve 42 is cannulated such that the sleeve 42 may be pulled over the cannula body 16 (i.e., the cannula body 16 extends through the sleeve 42, as shown in FIG. 8). This allows for a combination of materials to be used to achieve the same functionality of the cannula 10 in FIG. 1.

Figure 9:
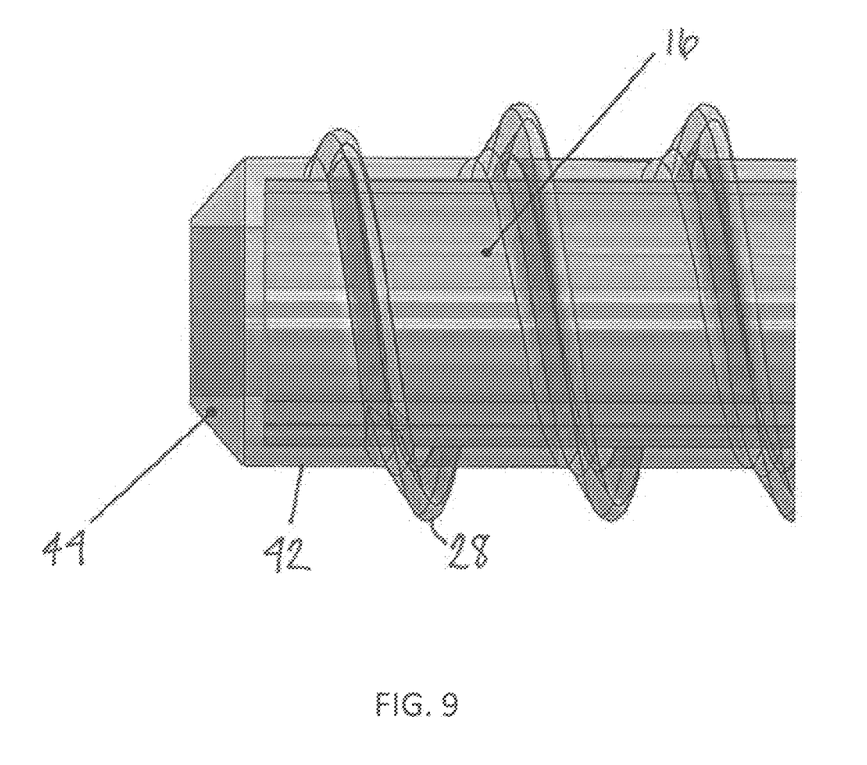
FIG. 9 is a partial interior view of the distal end of the cannula of FIG. 7.

Turning briefly to FIG. 9, there is shown a partial interior view of the distal end 14 of the cannula 10 of FIGS. 7 and 8. When the rigid cannula body 16 is extended through the flexible sleeve 42, the sleeve 42 extends distally past the distal body end 24 of the cannula body 16. This additional length of the sleeve 42 is a compliant tip 44, as shown in FIG. 9. The compliant tip 44 protects the surgical site from unintentional injury.

Figure 10:
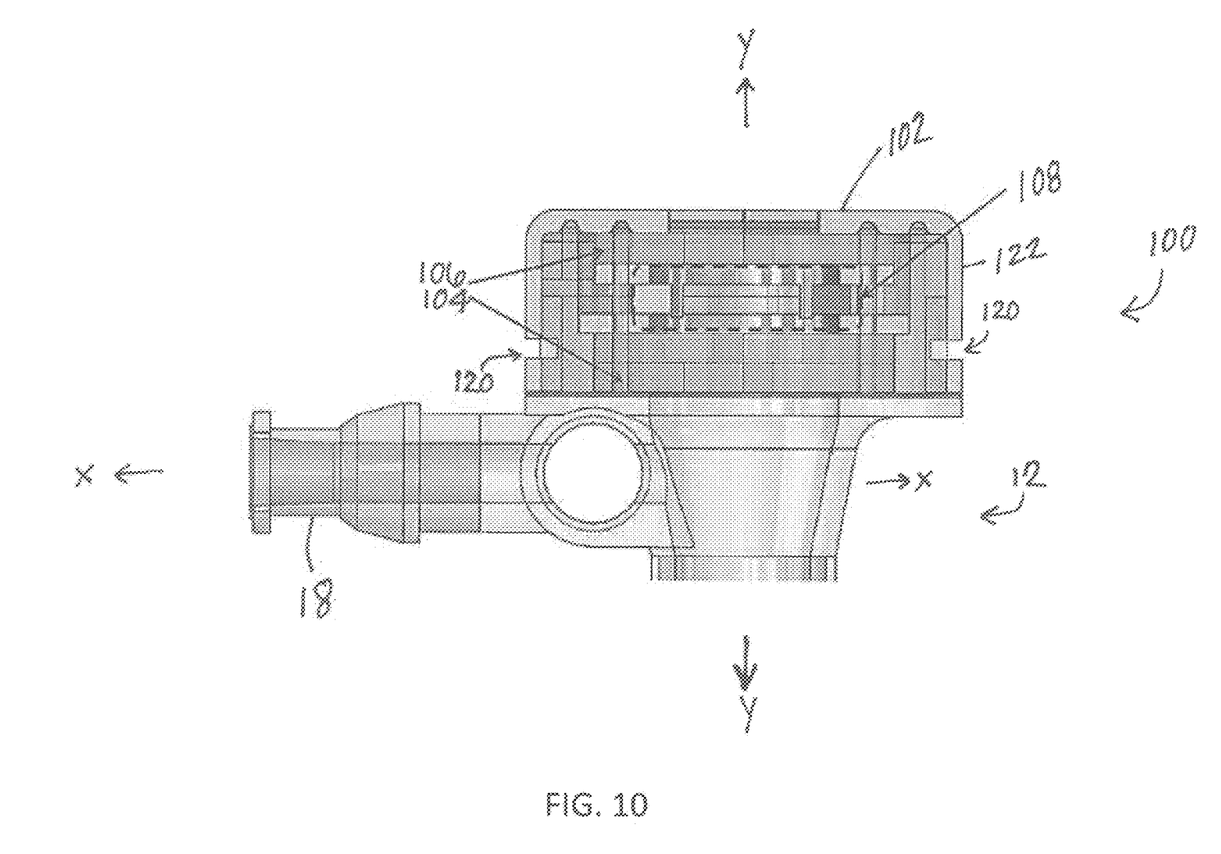
FIG. 10 is a partial interior side view schematic representation of a cannula seal assembly, according to an embodiment.

Referring now to FIG. 10, there is shown a partial interior side view schematic representation of a cannula seal assembly 100, according to an embodiment. The assembly 100 is sized and configured for attachment to the proximal end 12 of a cannula 10 (such as that shown in FIGS. 1 and 7-9). The assembly 100 comprises a housing 102 having two seals positioned therein. The two seals include: one or more distal primary seals 104 and a proximal secondary seal 106. As also shown in FIG. 10, a reservoir 108 separates the primary seal 104 from the secondary seal 106.

The primary seal 104 is the main seal within the assembly 100. Fluid flows through the cannula 10 from the distal body end 24 of the cannula body 16 toward the primary seal 104. When the primary seal 104 is undisturbed, it provides a barrier that limits fluid flow through the cannula 10. When the primary seal 104 is disturbed (e.g., by a surgical instrument), fluid passes through the primary seal 104 and into the reservoir 108. As shown in FIG. 10, the reservoir 108 is a space between the primary and secondary seals 104, 106. Any projectile leakage bypassing the primary seal 104 is captured by the secondary seal 106. The secondary seal 106 drastically reduces the amount of "splashing" experienced by the user. In particular, the secondary seal 106 serves as a splash guard because it does not withstand fluid pressure, but it captures projectile leakage.

Figure 11:
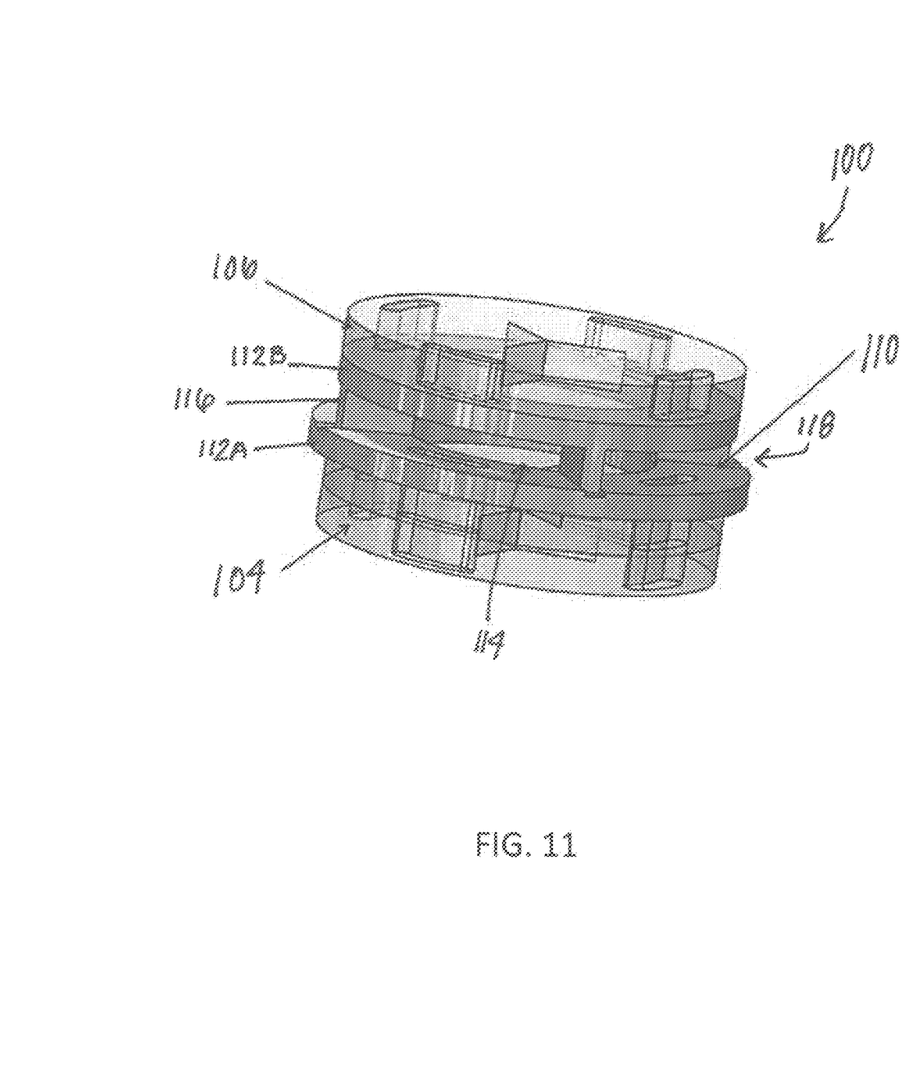
FIG. 11 is a partial interior perspective view schematic representation of the primary and secondary seals, according to an embodiment.

Turning now to FIG. 11, there is shown a partial interior perspective view schematic representation of the primary and secondary seals 104, 106, according to an embodiment. As shown, the separation of the primary seal 104 from the secondary seal 106 is maintained by a spacer 110. The spacer 110 is composed of circular disks 112A, 112B with a central aperture 114 to avoid interference with the reservoir 108. In the embodiment shown in FIG. 11, the spacer 110 comprises a first circular disk 112A and a second circular disk 112B with one or more connectors 116 extending therebetween. The connectors 116 can be any piece or portion of rigid material that holds the first circular disk 112A at a distance from the second circular disk 112B, creating at least one transverse spacer slot 118 therebetween. The purpose of the spacer slot(s) 118 is to allow fluid to flow out from the reservoir 108.

Over the course of use, the reservoir 108 between the primary seal 104 and the secondary seal 106 fills with fluid. The presence of low-pressure fluid in the reservoir 108 offers additional protection against projectile leakage. Any excess fluid will leak out from the reservoir 108 and through one or more transverse exterior slots 120 in an exterior wall 122 of the housing 102 (FIG. 10), preventing fluid buildup between the primary and secondary seals 104, 106. The spacer slots 118 and the exterior slots 120 are transverse to a central longitudinal y-y axis extending through the cannula 10. Specifically, the slots 118, 120 extend in a direction along (or substantially parallel to) an x-x axis that is substantially perpendicular to the central longitudinal y-y axis and substantially parallel to the direction of the extension of the port 18 (FIG. 10).

Figure 12:
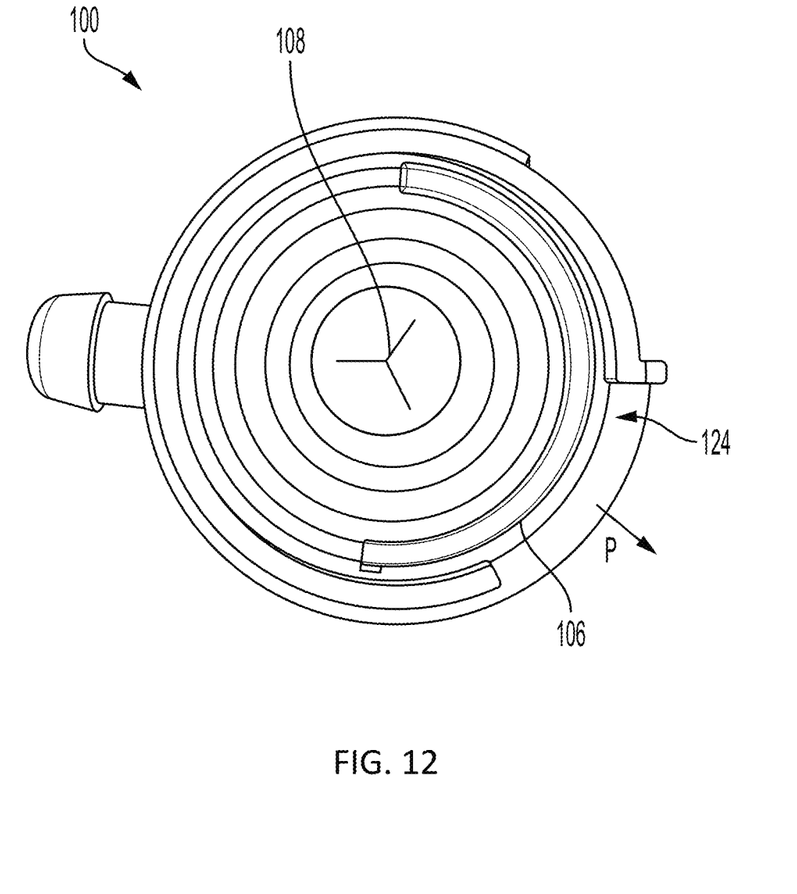
FIG. 12 is a top view schematic representation of the cannula seat assembly, according to an embodiment.
Figure 13:
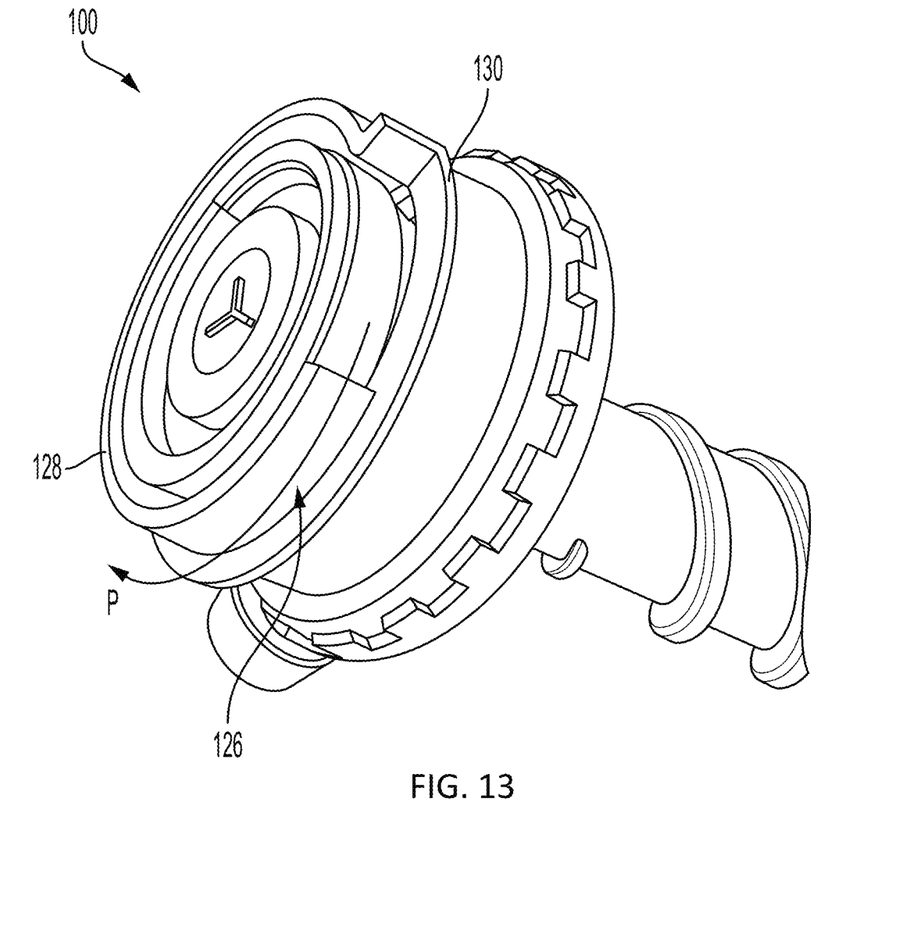
FIG. 13 is a perspective view schematic representation of the cannula seal assembly, according to an embodiment.
Figure 14:
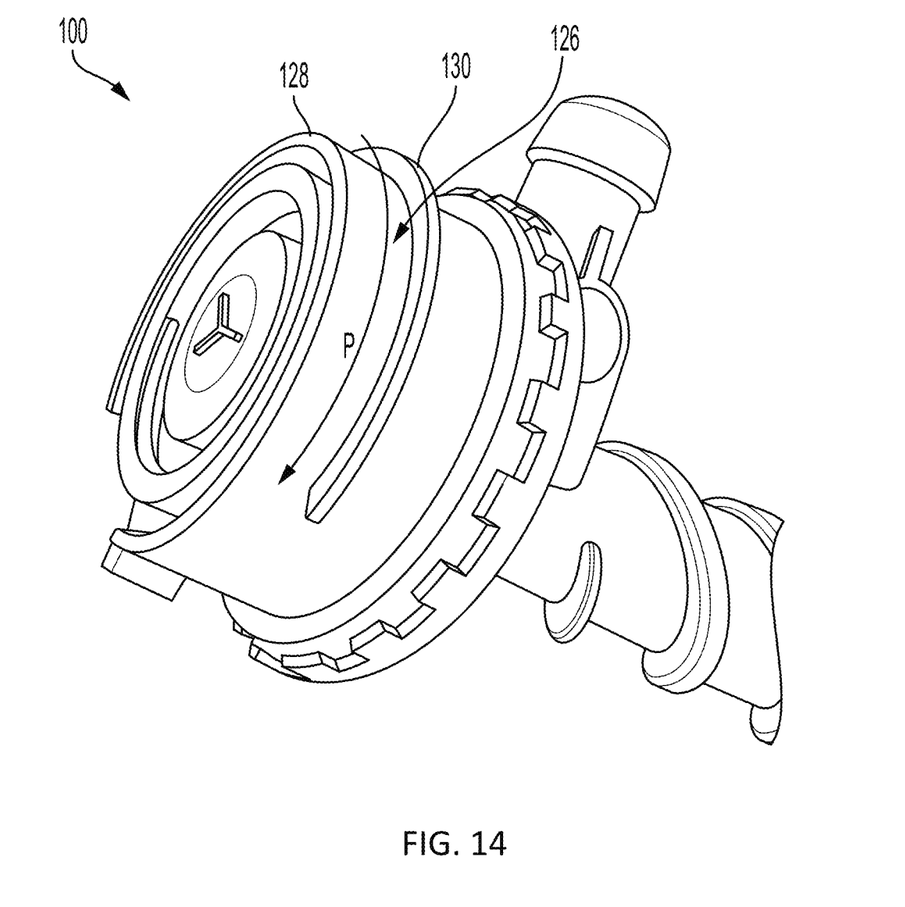
FIG. 14 is another perspective view schematic representation of the cannula seal assembly, according to an embodiment.

Referring now to FIGS. 12-14, there are shown various views schematic presentations of the cannula seal assembly 100, according to an embodiment. To ensure that the reservoir 108 is consistently filled with fluid to aid in leakage protection, the assembly 100 comprises one or more chambers 124 extending around the reservoir 108. As shown in FIG. 12, the chambers 124 are concentric, extending at least partially around the reservoir 108. In the depicted embodiment, the chamber 124 is created between the secondary seal 106 and the housing 102. (Note, the housing 102 has been removed in FIGS. 12-14 for clarity). Fluid levels between the primary and secondary seals 104, 106 rise as fluid enters through the primary seal 104. Eventually, fluid exceeds the volume of the reservoir 108 and flows out through the chamber 124.

As shown in FIGS. 13 and 14, the assembly 100 also comprises one or more channels 126 extending around the reservoir 108. In the depicted embodiment, the seals 104, 106 are concentrically surrounded by an interior wall 128. The interior wall 128 has one or more edges 130 extending therealong such that the edges 130 are between the interior wall 128 and the housing 102. The edges 130 create the channels 126 extending around the reservoir 108. In the depicted embodiment, the edge 130 and resulting channel 126 extend only partially around the reservoir 108. In addition, the channel 126 shown in FIGS. 13 and 14 is offset from the chamber 124 to ensure that the water level of the outflow always exceeds the height of the spacer 110.

Specifically, FIG. 12 shows the fluid path p out of the chamber 124. FIG. 13 shows the fluid path p out of the chamber 124 and into the channel 126. Fluid levels must exceed the peak before flowing out of the assembly 100. The offset configuration of the chamber 124 and the channel 126 in FIG. 14 ensures that a robust layer of fluid remains over the primary seal 104 in the reservoir 108. Ultimately, the configuration of the spacer 110 and seals 104, 106 allows the reservoir 108 to prime with fluid over the course of usage.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:
1. A cannula, comprising:
   an elongated rigid cannula body extending along a longitudinal axis and having a proximal body end and a distal body end;
   wherein the cannula body is composed of material having a first thickness;

a flexible thread extending along at least a portion of the cannula body from the distal body end toward the proximal body end; and wherein the thread is composed of material having a second thickness, which is less than a first thickness;

wherein:
  the thread comprises a tip, a base, and a triangular-shaped supporting feature, the base having a proximal side, a distal side, and the triangular-shaped supporting feature is positioned adjacent to the distal side and extends from the cannula body,
  the supporting feature shares a root portion with the thread, and includes an end portion opposite from the root portion, the end portion being spaced from the tip of the thread in a relaxed condition, and
  the root portion extends radially beyond an outside surface of the cannula body.

2. The cannula of claim 1, wherein the thread comprises a base having a distal side with a first radius and a proximal side with a second radius, and the second radius is smaller than the first radius.

3. The cannula of claim 1, wherein the supporting feature is angled, increasing in size toward the distal side of the thread.

4. A cannula, comprising:
  an elongated rigid cannula body having a proximal body end and a distal body end;
  a flexible sleeve extending along at least a portion of the cannula body from the distal body end toward the proximal body end; and
  a flexible thread extending along at least a portion of the sleeve;
  wherein:
    the thread comprises a tip, a base, and a triangular-shaped supporting feature, the base having a proximal side, a distal side, and the triangular-shaped supporting feature is positioned adjacent to the distal side and extends from the cannula body,
    the supporting feature shares a root portion with the thread and includes an end portion opposite from the root portion, the end portion being spaced from the tip of the thread in a relaxed condition, and the root portion extends radially beyond an outside surface of the cannula body.

5. The cannula of claim 4, wherein the cannula body is composed of material having a first thickness and the sleeve is composed of material having a second thickness, which is less than a first thickness.

6. The cannula of claim 4, further comprising a compliant tip on the flexible sleeve extending at least partially past the cannula body.

7. The cannula of claim 4, wherein the thread comprises a base having a distal side with a first radius and a proximal side with a second radius, and the second radius is smaller than the first radius.

8. The cannula of claim 4, wherein the supporting feature is angled, increasing in size toward the distal side of the thread.

* * * * *